Aug. 27, 1963 E. L. PAXMAN Plant Pat. 2,276
ALMOND TREE
Filed July 21, 1961
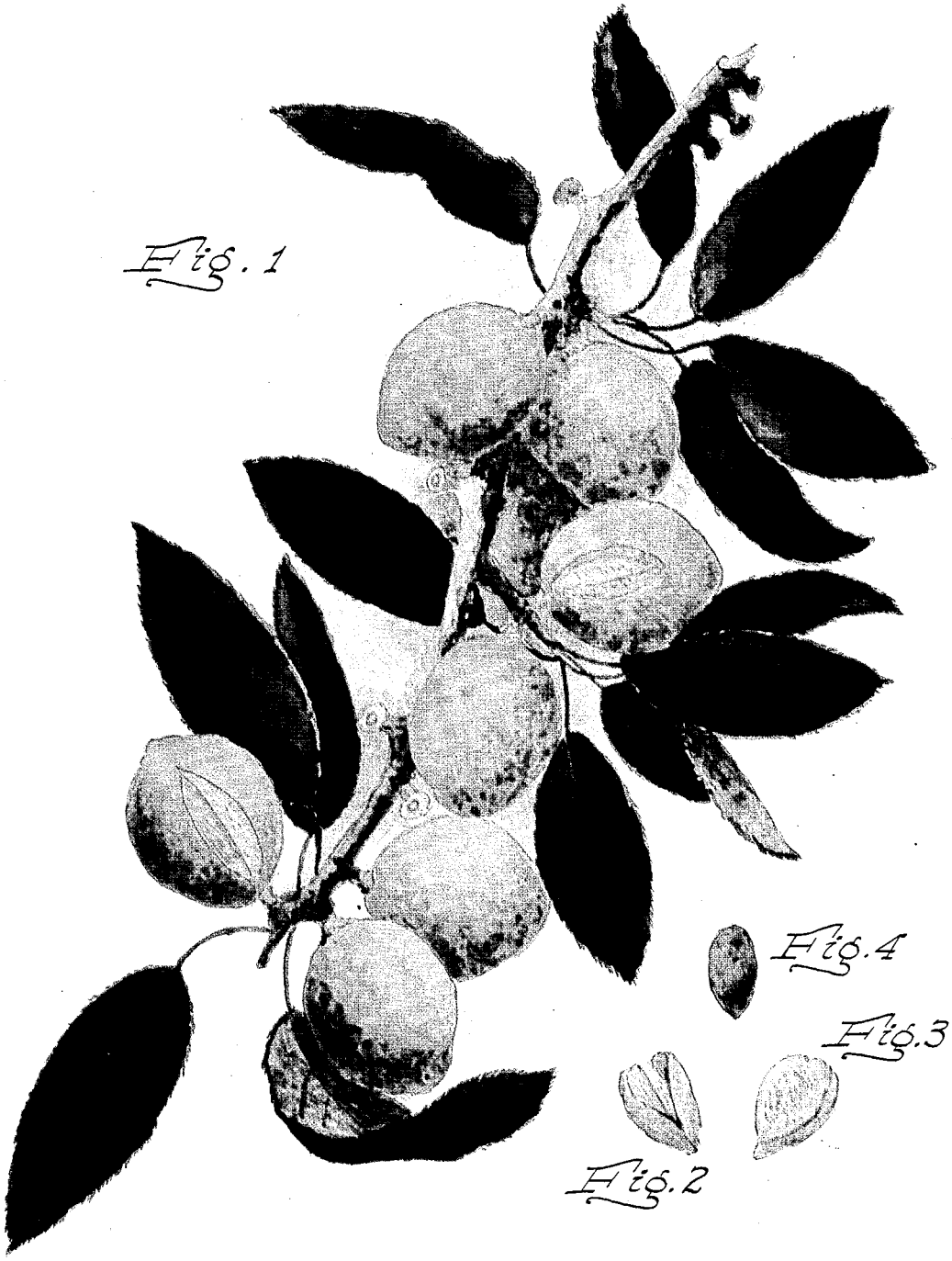
WITNESS
Addison E. Avery
INVENTOR
Edna L. Paxman
Webster & Webster
ATTYS.

United States Patent Office

Plant Pat. 2,276
Patented Aug. 27, 1963

2,276
ALMOND TREE

Edna L. Paxman, Rte. 1, Box 32, Ripon, Calif.

Filed July 21, 1961, Ser. No. 125,883
1 Claim. (Cl. Plt.—30)

This discovery relates to a new and distinct variety of almond tree which is characterized—as to novelty—by the consistent bearing of nuts which produce kernels of a small or "midget" size, and of a shape, especially desirable for use by the candy manufacturing industry; the nuts being soft shell, hulling and cracking easily, and better sealed than the Nonpareil (unpatented). The variety is in harvest relatively early; i.e., with or only slightly later than the Nonpareil.

The present variety of almond tree is believed to be a seedling, but its origin or parentage is unknown; the parent tree having been discovered by me in a family orchard located near Ripon, California.

Subsequent to recognition of the parent tree as a new and distinct variety—particularly by reason of the small size of the kernels of the nuts—such variety was first asexually reproduced on my behalf, and under careful observation, by the University of California in its Roeber test plot located near Winters, California. Such reproductions, accomplished by topworking, carry forward the distinctive characteristics of the parent tree, and run true in all essential respects.

In the drawings:

FIG. 1 is an elevation of a twig with leaves and nuts; certain of the nuts being shown with the hulls partially open.

FIG. 2 is a view of one of the nuts detached and with the hull substantially fully open.

FIG. 3 is a similar view but with the hull removed.

FIG. 4 is a view, substantially to size, of one of the kernels.

Referring now more specifically to the botanical details of this new and distinct variety of almond tree, the following is an outline description thereof; all major color plate identifications being by reference to Maerz and Paul Dictionary of Color, except where common terms of color definition are employed:

*Tree*

Density: Open.
Size: Large; tall; upright.
Vigor: Moderate.
Trunk:
- *Form.*—Medium to slender.
- *Texture.*—Smooth to medium.

Branches:
- *Form.*—Medium to slender.
- *Texture.*—Smooth to medium.
- *Branching habit.*—Medium to upright with the angles of the branches tending to be narrow.
- *Lenticels.*—Moderately prominent.
- *Color.*—On young twigs, green overlaid with brown. Whitish epidermal layer (21–A–1) cracking and sloughing off on two-year wood. Older wood becomes a brownish-orange or India Tan (7–A–12).

Foliage:
- *Abundance.*—Average, giving a somewhat open appearance.

- *Leaves.*—Size—medium; variable—on the average 2" to 3" in length and ¾" to 1" in width. Shape—lanceolate to elliptical with the tip acute but sometimes obtuse; some leaves tend to twist or spiral. Thickness—medium. Texture—smooth. Margin—serrulate. Petiole—medium thickness, and about one-third the length of the blade. Glands—usually two, rather indistinct, small, globose, and borne on base of blade. Color: top side—shiny, medium green (22–L–7); under side—dull, lighter green (22–J–5).

Bloom: Amount of bloom—average.

Crop:
- *Production.*—Medium to light, depending on weather conditions.
- *Distribution of nuts on tree.*—Borne on short spurs reasonably well distributed throughout the tree.
- *Harvest period.*—Relatively early, i.e., about with or slightly later than the Nonpareil.
- *Tenacity.*—Hang well on tree; easy to harvest; easy to hull.

Hull:
- *Shape.*—Regular. Oblong, with apical end rounded. Remnant of style persists at apical end.
- *Length.*—About 1⅓ the width.
- *Thickness.*—About 80% of the width.
- *Flesh.*—Relatively thin.
- *Suture.*—Narrowly depressed.
- *Dehiscence.*—Along suture only.
- *Pubescence.*—Densely covered with short white hairs.
- *Color.*—Green (19–K–2), shading to grey (22–A–1).

Nut:
- *Size.*—Small.
- *Form.*—Length/width — ovate. Width/thickness—medium.
- *Shell.*—Paper or soft shell; well sealed. Outer portion of shell generally completely retained on nut.
- *Color.*—Medium to light (10–E–5).
- *Pits.*—Medium to large; numerous; usually quite prominently rounded but sometimes irregular.
- *Base.*—Square. Stem scar—large; located directly on base end.
- *Apex.*—Acute; somewhat prolonged to tip.
- *Wing.*—Very prominent; broad; thin; extends full length of side from base to apex.
- *Inner surface.*—Light to medium color; neutral streak moderately dark.
- *Percent kernel to nut.*—60% to 70%.

Kernel:
- *Size.*—Small; average, approximately 35 to an ounce.
- *Form.*—Ovate; relatively flat for the size; evenly shaped on both sides with the widest part of the kernel very near the base. Ratio of width: length 55 to 60:100: thus, in relation to length, slightly broader than Nonpareil but not as broad as Drake or Mission (Texas); all unpatented.
- *Base.*—Tends to be round, with the two shoulders having about equal curvature. Base scar—relatively large.
- *Apex.*—Obtuse; relatively blunt, with short mucronate point.
- *Pellicle.*—Tan to light brown; covered with a network of very fine inconspicuous hairs.

*Number of doubles.*—Few.
*Flavor.*—Average.
*Quality.*—Average—well suited for commercial use, particularly candy bar manufacture.
*Color.*—Ivory white.

The tree and its nuts herein described may vary in slight detail due to climatic and soil conditions under which the variety may be grown.

The following is claimed:

A new and distinct variety of almond tree, as illustrated and described, characterized as to novelty by nuts whose kernels are relatively small, averaging 35 to an ounce; nuts borne on short spurs, hang well on the tree, and are well distributed thereon; soft shell nuts which are easy to harvest, hull, and crack; and nuts with a better seal than the Nonpareil but in harvest substantially with or slightly later than the same.

No references cited.